(12) United States Patent
Fowler et al.

(10) Patent No.: US 11,130,949 B2
(45) Date of Patent: Sep. 28, 2021

(54) GENE SILENCING

(71) Applicant: SYNGENTA PARTICIPATIONS AG, Basel (CH)

(72) Inventors: Jeffrey David Fowler, Greensboro, NC (US); Nema Devi Jhurry, Greensboro, NC (US)

(73) Assignee: SYNGENTA PARTICIPATIONS AG, Basel (CH)

(*) Notice: Subject to any disclaimer, the term of this patent is extended or adjusted under 35 U.S.C. 154(b) by 0 days.

(21) Appl. No.: 16/339,989

(22) PCT Filed: Sep. 19, 2017

(86) PCT No.: PCT/EP2017/073601
§ 371 (c)(1),
(2) Date: Apr. 5, 2019

(87) PCT Pub. No.: WO2018/065206
PCT Pub. Date: Apr. 12, 2018

(65) Prior Publication Data
US 2020/0040335 A1 Feb. 6, 2020

Related U.S. Application Data

(60) Provisional application No. 62/404,245, filed on Oct. 5, 2016.

(51) Int. Cl.
*A61K 48/00* (2006.01)
*C12N 15/11* (2006.01)
(Continued)

(52) U.S. Cl.
CPC ............ *C12N 15/111* (2013.01); *A01N 25/22* (2013.01); *A01N 63/60* (2020.01); *C12N 15/113* (2013.01);
(Continued)

(58) Field of Classification Search
CPC ................ C12N 15/111; C12N 15/113; C12N 2310/351; A01N 63/10
See application file for complete search history.

(56) References Cited

U.S. PATENT DOCUMENTS

2009/0182136 A1 7/2009 Wengel et al.
2010/0209440 A1 8/2010 Shankar et al.

FOREIGN PATENT DOCUMENTS

| AT | 534737 T | 12/2011 |
| EA | 015563 B1 | 8/2011 |
| WO | 03106636 A2 | 12/2003 |

OTHER PUBLICATIONS

Ragelle H. et al.; "Chitosan Nanoparticles for siRNA delivery: Optimizing Formulation to Increase Stability and Effiency"; Journal of Controlled Release, vol. 176; Dec. 31, 2013; pp. 54-63.
(Continued)

*Primary Examiner* — Terra C Gibbs
(74) *Attorney, Agent, or Firm* — Syngenta Participations AG; Toni-Junell Herbert (57) ABSTRACT

The present invention provides for methods of delivering polynucleotides to subterranean plant pests. In particular, the present invention relates to methods of reducing the binding of a composition, comprising polynucleotide and a cationic polymer, to soil by substantially quenching positively charged residues with a quenching agent. The invention also comprises compositions comprising a cationic polymer, a polynucleotide and a quenching agent.

7 Claims, 6 Drawing Sheets

(51) Int. Cl.
*C07H 21/02* (2006.01)
*C07H 21/04* (2006.01)
*A01N 25/22* (2006.01)
*C12N 15/113* (2010.01)
*A01N 63/60* (2020.01)

(52) U.S. Cl.
CPC .... *C12N 2310/14* (2013.01); *C12N 2310/351* (2013.01); *C12N 2320/32* (2013.01); *C12N 2320/51* (2013.01)

(56) References Cited

OTHER PUBLICATIONS

Ewe Alexander et al.: "Optomized Polyethylenimine (PEI)-based Nanoparticles for siRNA delivery, Analyzed in Vitro and in an Ex Vivo Tumor Tissue Slice Culture Model"; Drug Delivery and Translational Research, vol. 7, No. 2, Jun. 22, 2016; pp. 206-216.
Arkadi Zintchenko et al.; "Simple Modifications of Branched PEI Lead to Highly Efficient siRNA Carriers with Low Toxicity"; Bioconjugate Chem; Jun. 14, 2008; pp. 1448-1455.
Samuel Dubelman et al.; "Environmental Fate of Double-Stranded RNA in Agricultural Soils"; PLOS ONE; vol. 9, No. 3; Mar. 27, 2014; p. e93155.
International Search Report from corresponding PCT Application No. PCT/EP2017/073601; dated Dec. 13, 2017; 2 pgs.
Arkadi Zintchenko et al.; "Simple Modifications of Branched PEI Lead to Highly Efficient siRNA Carriers with Low Toxicity"; Bioconjugate Chem; Jun. 14, 2008; pp. 1448-1455 and supporting information.
Written Opinion of the International Searching Authority in PCT Application No. PCT/EP2017/073601 dated Dec. 13, 2017.

GENE SILENCING

CROSS-REFERENCE TO RELATED APPLICATIONS

This application is a 371 National Stage application of International Application No. PCT/EP2017/073601, filed Sep. 19, 2017, which claims priority to U.S. Provisional Application No. 62/404,245 filed Oct. 5, 2016, the entire contents of which applications are hereby incorporated by reference.

The present invention relates to control of gene expression by double stranded RNA. In particular the invention relates to a method of enhancing the ability of double stranded RNA administered exogenously—i.e. external to a target organism and under relatively harsh environmental conditions—to silence gene expression in that organism. The invention also relates to compositions for use in the method, and to the use in the method of known agents which "quench" positive charge in a complex comprising a polynucleotide, in particular dsRNA, and a cationic polymer.

The phenomenon of RNA interference potentially to silence gene expression is well known.

RNA is relatively unstable and can be rapidly degraded by, for example, ribonucleases which are ubiquitously present even outside of cells. A problem with the application of dsRNA either directly to target organisms, or via exogenous administration to a locus at which they exist concerns the poor stability of the RNA.

By exogenous application is meant applied to the target organism in such a way that the organism can incorporate it, or that the dsRNA is produced in a first organism which is different from the target organism and that the target organism incorporates the first organism, or a part thereof comprising the dsRNA so that—either way—the said dsRNA is capable of effecting post-transcriptional silencing of a gene comprising a nucleotide sequence corresponding to that comprised by the dsRNA.

Exogenous application is distinguished from endogenous production—by which is meant production (generally via expression from an appropriate heterologous sequence) in the cells of the target organism of a double stranded RNA capable of post-transcriptionally silencing targeted genes.

Whilst the exogenously applied dsRNA is generally capable of exerting a relevant biological effect within the short term, perhaps even for up to a few days after application, the effect generally rapidly declines with the dsRNA typically having a half-life less than about 12 to 24 hours in soil for example, and further depending on the precise environmental conditions in which it is administered.

Various solutions to this problem have been proposed, including stabilising the dsRNA by encapsulating or otherwise binding it to a polymer which enhances its stability, thus providing for an increased duration of action. Such a stabilised dsRNA is not without its own problems, however, insofar as a complex formed between it and a cationic polymer may be bound by, or otherwise binds to, charged particles present in or at the locus which reduces its availability or impedes the movement of the complex through the locus and typically to the site at which the target organism is located. This problem is exacerbated by the movement of the target organisms away from the site at which the dsRNA is initially applied.

The present invention is thus concerned with a solution to the problem of on the one hand stabilising dsRNA sufficiently to enable it to exert the desired biological effects, and on the other enabling the thus stabilised dsRNA to remain available or move or be moved within a locus at or in which the target organism is located.

According to the present invention there is provided a method of inhibiting or substantially reducing the binding of a composition, comprising a complex formed between a cationic polymer and a polynucleotide, to negatively charged molecules present in soil comprising including in the composition a quenching agent capable of substantially neutralising positive charges on the complex In a particularly preferred embodiment of the composition of the invention, the polynucleotide is a dsRNA, the polymer is a polyamine and the quenching agent is a mono-aldehyde or a monoepoxide.

In particularly preferred embodiment of the invention, the polymer is a linear or branched polyethyleneimine, polypeptide or cationic polysaccharide.

In particularly preferred embodiment of the invention, the polymer is a linear or branched polyethyleneimine.

In particularly preferred embodiment of the invention, the negatively charges particles comprise humic acid.

The present invention also provides for method of controlling a subterranean plant pest infestation comprising providing;
a) a composition comprising a complex formed between a cationic polymer and a dsRNA,
b) substantially neutralising exposed-surface positive charges of the complex of a) with a quenching agent and
c) applying the composition of b) to the soil,
wherein the dsRNA effects post-transcriptional silencing of a target gene in said subterranean plant pest.

Subterranean plant pests include those pests that reside in the soil for at least a portion of their life cycle, for example the larval stage.

Subterranean pests include those from the group consisting of *Diabrotica virgifera virgifera* (Western corn rootworm), *Diabrotica barberi* (Northern corn rootworm), *Diabrotica undecimpunctata howardi* (Southern corn rootworm), *Diabrotica virgifera zeae* (Mexican corn rootworm), *Diabrotica speciosa* (cucurbit beetle), nematodes, wireworms and grubs and appropriate soil pathogens such as bacteria and fungi.

Preferably, the subterranean pest is a *Diabrotica* species.

The invention also provides the use of a quenching agent to substantially neutralise residual positively charged groups in a complex comprising a polynucleotide and a cationic polymer.

The present invention also provides a composition comprising a complex formed between a cationic polymer and a polynucleotide, and a quenching agent capable of substantially neutralising residual exposed-surface positively charged groups on the complex, wherein the polymer is selected from the group consisting of branched or linear polyethyleneimine, imidazole containing polymers, chitosans, cationic polysaccharides, polyamidoamines, polymers and copolymers of amino acids such as lysine, histidine and arginine which comprise amine groups, and polyamines.

In a particularly preferred embodiment of the invention, the cationic polymer present in the composition is branched or linear polyethyleneimine.

By complex is meant a molecular entity formed by loose association involving two or more component molecular entities (ionic or uncharged).

When a cationic polymer and a polynucleotide form a complex, the net negative charge on the polynucleotide may be insufficient to counter-act or "neutralise" all the exposed-surface positively charged groups on the cationic polymer with the result that the complex comprises residual exposed-surface positively charged groups.

The polynucleotide of the invention may be an RNA. The RNA may be a dsRNA but it may also be a siRNA, miRNA or any other RNA molecule capable of RNAi gene silencing. Preferably the polynucleotide is a dsRNA.

Preferably, the dsRNA comprises at least 15 at least 16, at least 17, at least 18, at least 19, at least 20, at least 21, at least 22, at least 23, at least 24, at least 25, at least 30, at least 35, at least 40, at least 45, at least 50 or more nucleotides that are identical or complementary to a target gene in a target organism.

Suitable target genes are those in which post-transcriptional silencing has a detrimental effect on the target organism. For example, altering growth, stunting, increased mortality, decrease in reproductive capacity or decreased fecundity, decrease in or cessation of feeding behaviour or movement, or decrease in or cessation of metamorphosis stage development.

The cationic polymer may be selected from the group consisting of branched or linear polyethyleneimine, imidazole containing polymers, chitosans, cationic polysaccharides, polyamidoamines, and polymers of amino acids such as lysine and arginine which comprise tertiary amino groups. Alternatively, the cationic polymer may be a polyamine, or a branched polyamine comprising at least 5 amine groups. Simple polyamines, such as spermine, spermidine, putrescine and cadaverine are not particularly preferred in the case that the polynucleotide is a dsRNA because use of a quenching agent to neutralise any residual charge on a complex formed between such a simple polyamine and dsRNA can cause the complex to disassociate.

In a preferred embodiment of the composition, the complex is comprised in a cell lysate or is formed within intact cells and the quenching agent is added thereto.

In terms of the quenching agent—anything which contains a single group which is capable of reacting with an amine to quench a positive charge on it is sufficient, although some agents are preferred, including isocyanates, mono-epoxides, mono-esters, mono-carboxylic acids, mono-anhydrides, mono-aldehydes and pyrocarbonates.

However, a particularly preferred quenching agent is a mono-aldehyde or monoepoxide. The mono-aldehyde may be water soluble or water insoluble. Water soluble mono-aldehydes present in the composition of the invention include methanal, ethanal, propanal, butanal, pentanal and hexanal. Preferred water-insoluble mono-aldehydes include heptanal, octanal, and decanal. Preferred monoepoxides include polyethylene glycol glycidyl ether with a degree of polymerization ranging from 1 to about 10.

The quenching agent should be present in the composition in an amount sufficient to substantially quench any residual exposed-surface positively charged groups in the complex, such that the complex substantially does not bind to negatively charged particles such as are present in soil, of which humic acid is an example. The skilled formulation chemist is in a position easily to determine what these amounts are, but typically they are present in the composition in an amount such that the number of moles of monovalent quenching agent is equal to from about 10% to about 190% of the number of moles of amine present in the complex (recognising that primary amines are divalent for quenching reactions whereas secondary amines are monovalent).

In the case that the polynucleotide is a dsRNA, it comprises a sequence which is substantially identical to the sequence of an mRNA of a gene in a eukaryotic cell. In particular the eukaryote may be an insect selected from the group consisting of *Diabrotica virgifera virgifera* (Western corn rootworm), *Diabrotica barberi* (Northern corn rootworm), *Diabrotica undecimpunctata howardi* (Southern corn rootworm), *Diabrotica virgifera zeae* (Mexican corn rootworm), *Diabrotica speciosa* (cucurbit beetle), nematodes, wireworms and grubs and appropriate soil pathogens such as bacteria and fungi. Neutralisation of residual positive charge in a complex comprising a polynucleotide and a cationic polymer enables the complex to move more freely on or through a substrate which contains negative charges—to which the complex is applied.

It is well known that control of corn root worms is not necessarily wholly effective if a composition comprising an insecticidal agent is applied to locus which comprises root worm larvae as part of a soil drench. One possible reason is that availability or movement of the insecticidal composition through the soil may be impeded by electrostatic and/or other binding interactions between the active ingredient and/or the insecticidal formulation as a whole and charged components of the soil to which it is applied. By availability is meant that the active ingredient remains in the water phase of the soil, instead of adsorbed to solid components. The invention will be further apparent from the following non limiting example(s) . . . .

The following abbreviations are used: –% w/w=percentage as a function of total weight ODU=optical density units (absorbance at 600 nm)

PBS buffer=Phosphate Buffered Saline buffer

BPEI 25 kD=branched polyethyleneimine of molecular weight 25 kD (25000 g/mol)

EXAMPLE 1

Control sample A. 10 μL of IVT dsRNA at nominal 1 mg/mL was combined with 13 μL of 10% solution of bPEI (branched polyethyleneimine) 60 kDa in PBS buffer. This was diluted to 500 μL total volume in PBS, then combined with 10 mg colloidal silica [Aerosil 200, Evonik]. The sample was spun briefly in a centrifuge at 2000 rpm and the supernatant collected. 1 μL of 1% heparin. Na salt was added to de-complex any bPEI-dsRNA. When run on an electrophoresis gel no band was visible corresponding to the dsRNA, indicating that all of the complex had bound to the colloidal silica.

Test sample B. This sample was prepared in the same way as control sample A, except that before combining with colloidal silica, 25 μL of a quench pentanal 10% solution in PBS buffer was added and allowed to react under ambient conditions for 1 hour. In this case a band was visible corresponding to free dsRNA and the band intensity indicated that about 25% of the total dsRNA had not bound to the colloidal silica in the form of bPEI-dsRNA complex.

EXAMPLE 2

PEI (=Polyethyleneimine) coated cells may improve stability of dsRNA in soil. However, PEI coating of cells may cause the cells to adsorb strongly to soil due to interaction of amine groups to acid groups in soil. This may impair soil mobility and delivery of the dsRNA to CRW. By reacting the PEI coat with glutaraldehyde or monoaldehyde (pentanal), the free amine groups on the PEI may be quenched so that their interaction with soil is reduced. However, quenching with glutaraldehyde leads to some degree of flocculation, which may impair soil mobility. As shown below, monoaldehyde treatment does not lead to flocculation, and may therefore be a preferred way to quench the free amines.

1. Intact cells (previously treated with 0.002% w/w per ODU glutaraldehyde and then washed) were resuspended at 12 ODU/mL in PBS buffer and divided into 1 mL aliquots.
2. BPEI 25 kD solutions were prepared at 2% w/w BPEI (pH ~11) and at 1.25% w/w BPEI (pH~7).
3. Each intact cell aliquot was treated as follows with BPEI solutions, and observations recorded:
    Aliquot 1: Added BPEI (pH 11) to 0.1% w/w final BPEI concentration, then treated with 0.2% glutaraldehyde. Immediate severe flocculation was observed.
    Aliquot 2: Added BPEI (pH 11) to 0.1% w/w final BPEI concentration, then treated with 0.2% pentanal. No flocculation was observed.
    Aliquot 3: Added BPEI (pH 7) to 0.1% w/w final BPEI concentration, then treated with 0.2% glutaraldehyde. Immediate flocculation was observed, not as severe as aliquot 1, particle size of flocs was smaller as assessed visually.
    Aliquot 4: Added BPEI (pH 7) to 0.1% w/w final BPEI concentration, then treated with 0.2% pentanal. No flocculation was observed.

EXAMPLE 3

Modification of Polyethyleneimine (PEI)
PEGylation of PEI by epoxy-functionalized PEG PEG-diglycidyl ether (500D) was first quenched with Tris-HCl (pH7) to target quenching of half of the epoxy groups in the di-functionalized PEG, to yield a mono-functionalized PEG. This was done by mixing PEG-diglycidyl ether of 20% Tris-HCl solution (pH 7) in a ratio targeting reaction with half of the epoxy groups on the PEG, followed by overnight incubation at elevated temperature. The mon-functionalized PEG thus obtained was mixed with branched PEI solution (adjusted to pH 7) in ratios targeting various levels of PEGylation of the primary amines on the PEI (nominally targeting 30%, 60% and 90% quenching of the primary amines). The actual degree of quenching of primary amines on the PEI was determined by performing a colorimetric TNBSA (2,4,6-trinitrobenzene sulfonic) assay. The actual PEGylation levels obtained were as follows (Table 1) and as expected are somewhat different from the nominal target for several possible reasons, including that the conversion of di-functional PEG to mono-functional was not a specific reaction, and because of steric hindrance blocking availability of the primary amines. The difference between nominal and actual degree of quenching does not affect the outcome of the experiment because it was designed to span a range of actual degree of quenching.

TABLE 1

| Targeted quenching of PEI primary amines | Measured quenching of PEI primary amines |
|---|---|
| 30% | 11% |
| 60% | 28% |
| 90% | 22% |

Modification of PEIs by Diethylpyrocarbonate

Primary amines on PEI were quenched by reaction with diethylpyrocarbonate (DEPC) by direct addition of DEPC to PET solutions adjusted to pH 7 to target varying levels of quenching of primary amines by DEPC (notably targeting 25%, 50% and 75% quenching). The actual degree of quenching of primary amines on the PEI was determined by performing a colorimetric TNBSA (2,4,6-trinitrobenzene sulfonic) assay. The actual levels of DEPC modification measured were as follows (Table 2), and as discussed above the discrepancy between targeted and actual degree of quenching does not affect the outcome of the experiment.

TABLE 2

| Targeted quenching of PEI primary amines | Measured quenching of PEI primary amines |
|---|---|
| 25% | 30% |
| 50% | 40% |
| 75% | 50% |

EXAMPLE 4

Evaluating Binding Affinities of Modified Vs. Unmodified PEI to Soil

Figure 1:
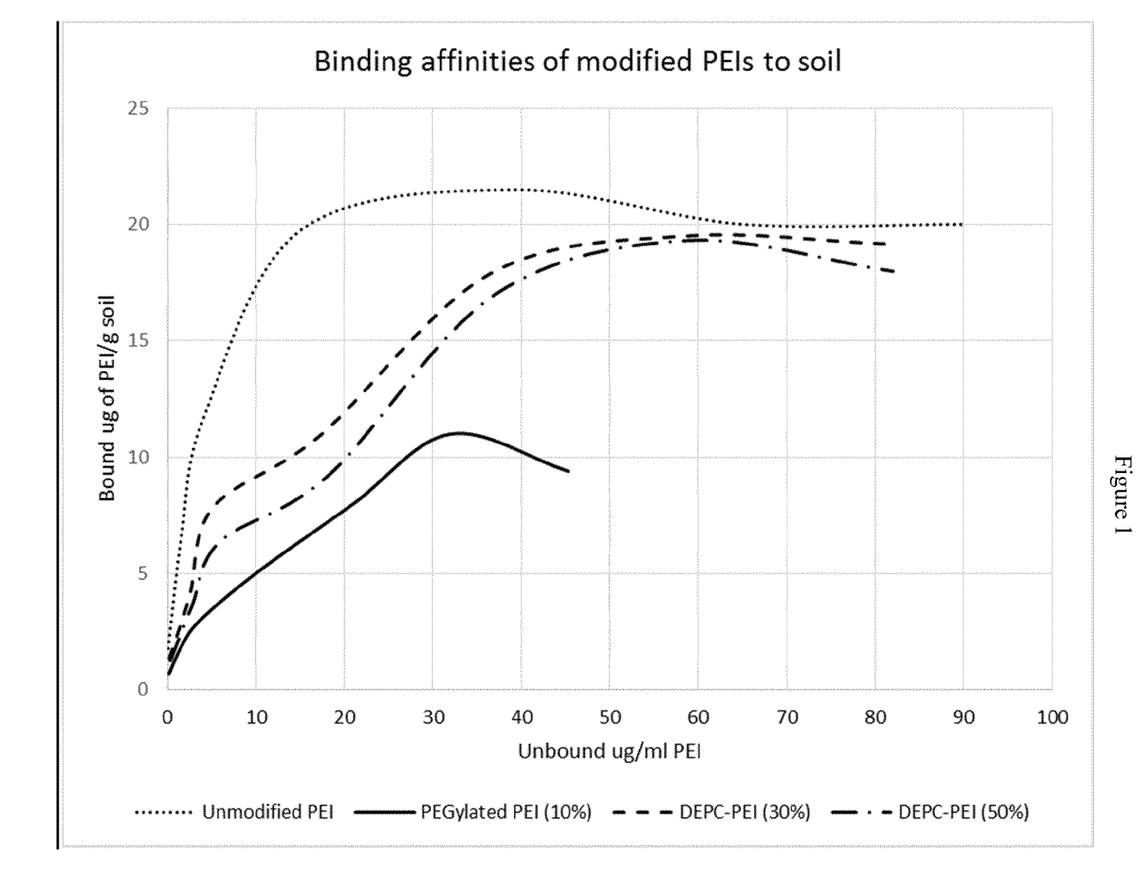
FIG. 1. Both PEGylated and DEPC-treated PEIs have lowered binding affinities compared to unmodified PEI.

Unmodified PEI solutions and solutions of PEI modified by PEGylation or DEPC were incubated with soil in a ratio of 2:1 (solution: soil) wt/wt for 1 hour. The concentrations of solutions tested varied from 0-0.08% of PEI. After soil incubation, the soil was separated from the PEI solutions by centrifugation. The unbound PEI remaining in the solution was assessed by the TNBSA assay. The binding profile of the PEI to soil was represented by binding isotherms (FIG. 1.). The level of primary amine quenching on the PEI is indicated the numbers in parentheses in the legend.

EXAMPLE 5

Binding Affinity of dsRNA-PEI Complexes

Figure 2:
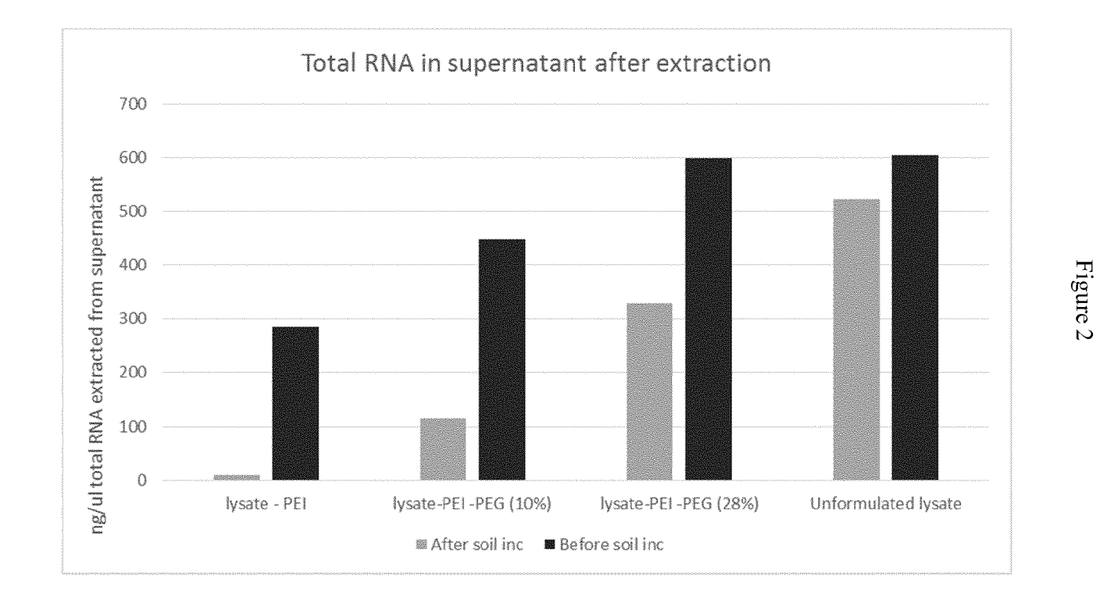
FIG. 2. Complexes made with PEGylated PEIs bind less strongly to soil, hence remain in the supernatant after soil incubation. The higher the degree of PEGylation, the lower the binding affinity of the complex to soil.

E. coli cell lysate expressing dsRNA was mixed with PEI solutions as follows: lysates were diluted to 25 OD/mL and PEI solutions were added to a final concentration of 0.75% to the lysates. The lysate dsRNA-PEI complex solutions were further diluted 2.5-fold and incubated with soil in a 2:1 solution: soil wt/wt ratio for 1 hour. Unformulated lysate solution was used as a control. The soil was subsequently pelleted by centrifugation and the unbound total RNA in the supernatant was extracted from the complexes by addition of a poly-anion to decomplex the dsRNA from the PEI, followed by RNAZol RT extraction. The total RNA concentration present in the supernatant of the samples was quantified by UV-Vis spectroscopy (FIG. 2.).

EXAMPLE 6

Evaluating Stability of Lysate-dsRNA in Complexes Made with Modified PEIs

Figure 3:
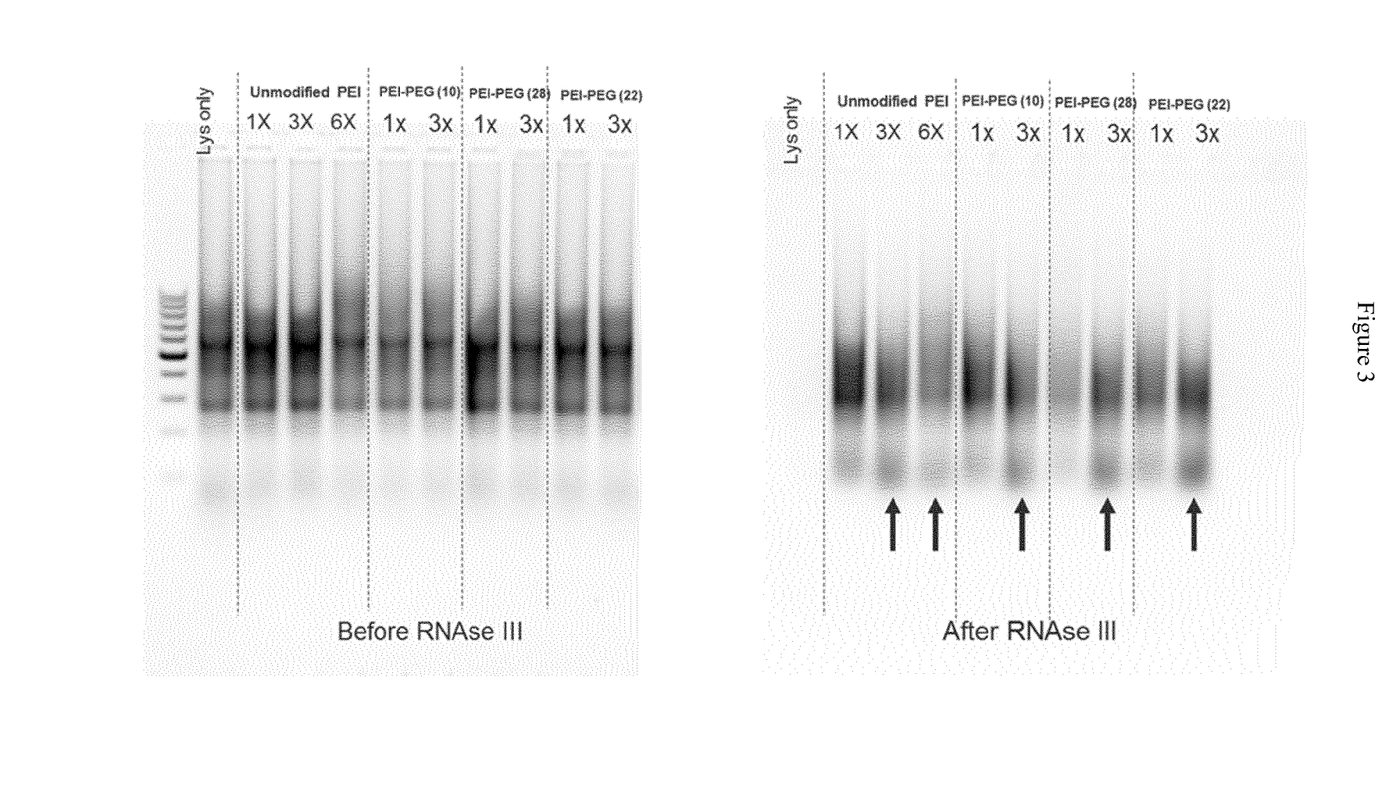
FIG. 3. Stability of lysate dsRNA in complexes made with modified PEIs (PEGylated PEIs). dsRNA is stable in complexes made with PEGylated PEIs.
Figure 4:
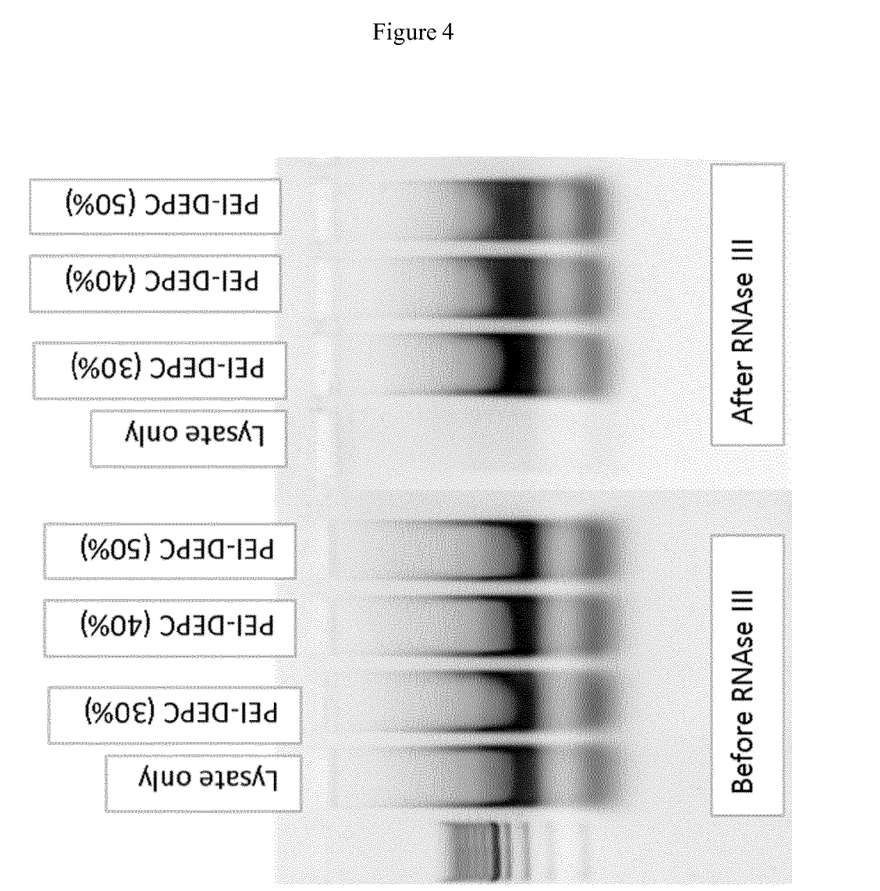
FIG. 4. Stability of lysate dsRNA in complexes made with modified PEIs (DEPC-treated PEIs). dsRNA is stable in complexes made with DEPC-treated PEIs.

E. coli cell lysate expressing dsRNA was mixed with PEI solutions as follows: lysates were diluted to 50 OD/mL and PEI solutions were added to a final concentration of 0.5% (1×PEI) or 1.5% (3×PEI) to the lysates. The lysate dsRNA-PEI complex solutions were incubated with RNAse III overnight at 37° C. Total RNA was extracted from the complexes by addition of a poly-anion to decomplex the dsRNA from the PEI, followed by RNAZol RT extraction. The integrity of the dsRNA was evaluated using agarose gel electrophoresis (FIGS. 3 and 4.)

EXAMPLE 7

Evaluating Bioavailability of dsRNA in Complexes Made with Modified PEIs

Figure 5:
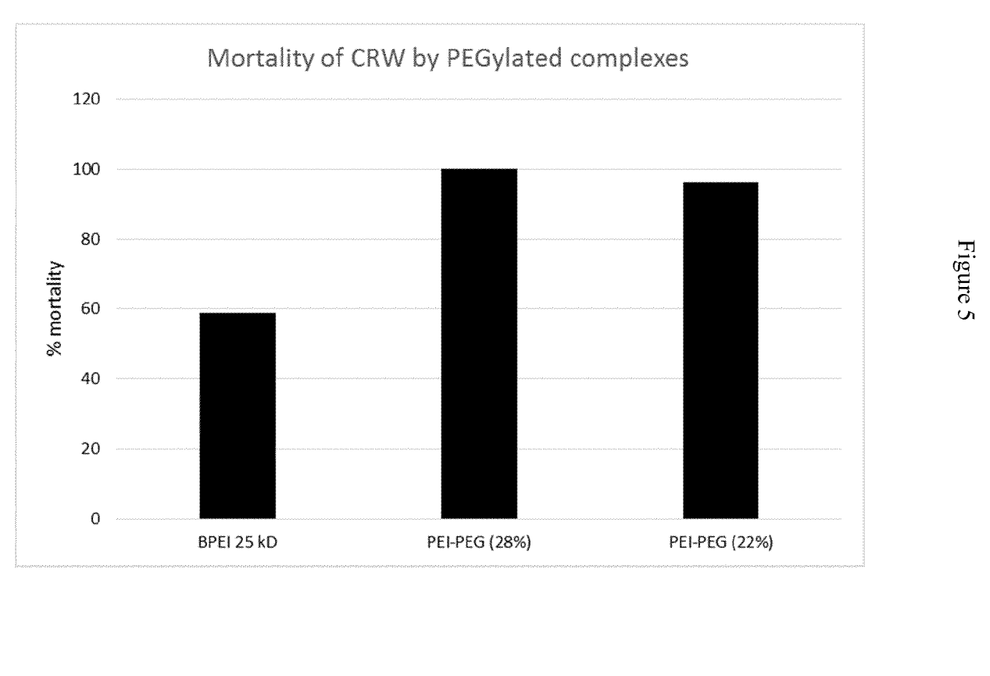
FIG. 5. Mortality of CRW is improved when dsRNA is complexed with PEGylated PEI, as compared to complexes made with unmodified PEI, showing improved bioavailability of the dsRNA in modified complexes.
Figure 6:
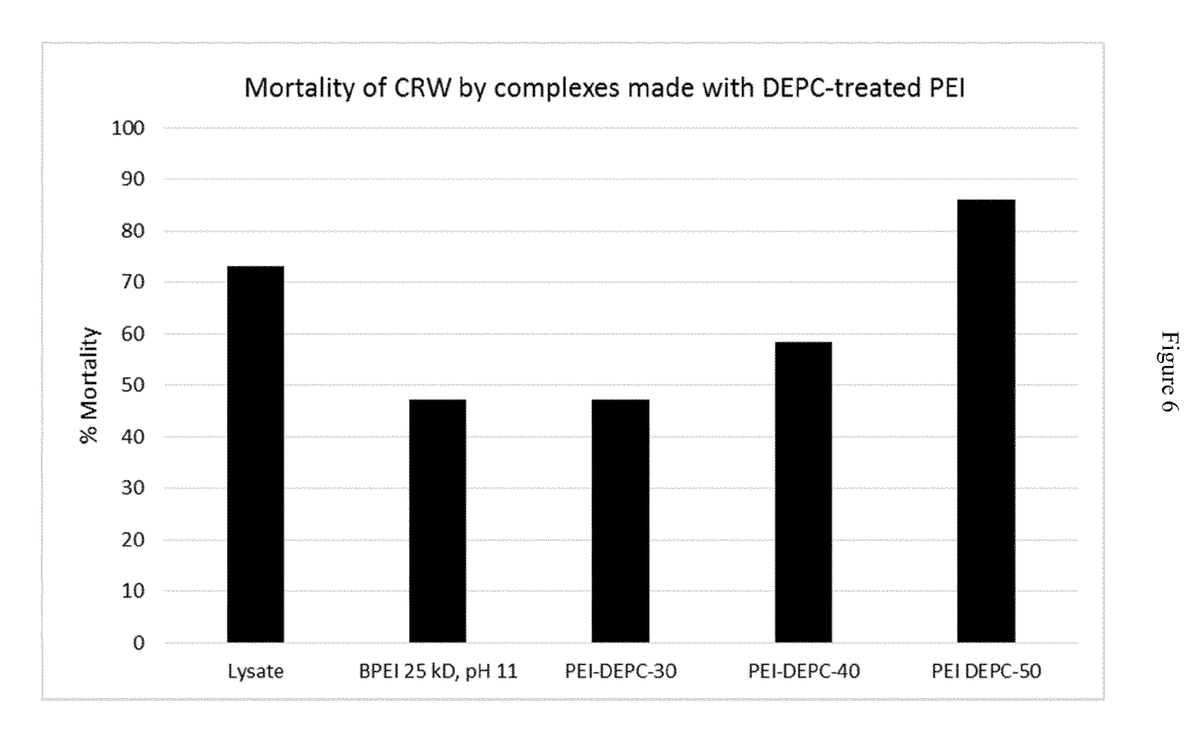
FIG. 6. Mortality of CRW is improved when dsRNA is complexed with DEPC-PEI, as compared to complexes made with unmodified PEI, suggesting improved bioavailability of the dsRNA in modified complexes. Higher modification levels on the PEI le

Artificial western corn rootworm diet-incorporation bioassay was conducted on the complexes made with the modified PEIs and the *E. coli* lysate expressing dsRNA. The lysate formulations were diluted using RNAse free water and mixed very well with equal amount of the diet (0.5 ml diet and 0.5 ml diluted formulation solutions) by vortex-mixing until homogeneous. Three replicates were conducted for each formulation type and for each replicate plate, approximately 12 neonatal larvae were added. Plates were incubated at room temperature. Mortality was recorded every other day for the duration of the assay. The final mortality rates are represented in FIGS. 5 and 6 and show improved activity of the quenched complexes This finding was also confirmed by bioassay in soil.